(12) United States Patent
Lal et al.

(10) Patent No.: US 6,242,645 B1
(45) Date of Patent: Jun. 5, 2001

(54) THERMALLY STABLE AMINOSULFUR TRIFLUORIDES

(75) Inventors: Gauri Sankar Lal, Whitehall; Guido Peter Pez, Allentown; Reno Joseph Pesaresi, Jr., Easton; Robert George Syvret, Allentown, all of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/535,682

(22) Filed: Mar. 23, 2000

Related U.S. Application Data

(62) Division of application No. 08/939,635, filed on Sep. 29, 1997.

(51) Int. Cl.[7] .......................... C07C 17/013; C07C 29/62
(52) U.S. Cl. .......................... 564/102; 540/591; 544/105; 548/469; 548/542; 558/460; 560/227; 570/127; 570/124; 570/131; 570/142; 570/144; 562/822
(58) Field of Search .......................... 558/460; 560/227; 570/127, 124, 131, 142, 144; 564/102; 562/822; 540/591; 544/105; 548/469, 542

(56) References Cited

U.S. PATENT DOCUMENTS

| | | | |
|---|---|---|---|
| 3,410,669 | * 11/1968 | Cramer et al. | 23/357 |
| 3,499,030 | 3/1970 | Kuhle et al. | 260/551 |
| 3,914,265 | 10/1975 | Middleton | 260/397 |
| 3,976,691 | 8/1976 | Middleton | 260/544 |

FOREIGN PATENT DOCUMENTS 433136   12/1974   (RU) .

OTHER PUBLICATIONS

Hann et al., J. Chem. Soc., Chem. Comm., (21), 1650–1, cited in Chem. Abst. 112:235107, 1989.*

W.J. Middleton, New Fluorinating Reagents. Dialkylaminosulfur Fluorides, *J. Org. Chem.*, vol. 40, No. 5, (1975), pp. 574–578.

Messina, et al., Aminosulfur Trifluorides: Relative Thermal Stability, *Journal of Fluorine Chemistry*, 43, (1989), pp. 137–143.

M. Hudlicky, Fluorination with Diethylaminosulfur Trifluoride and Related Aminofluorosulfuranes, Organic Reaction, vol. 35, (1988), pp. 513–553.

G. L. Hann, et al. Synthesis and Enantioselective Fluorodehydroxylation Reactions of (S)–2–(Methoxymethyl(pyrrolidin–1–ylsulphur Trifluoride, the First Homochiral Aminofluorosulphurane, J. Chem. Sol., Chem. Commun. (1989) pp. 1650–1651.

J. Cochran, Laboratory, Explosions, Chemical and Engineering News, (1979), vol. 57, No. 12, pp. 4 & 74.

W.T. Middleton, Explosive Hazards with DAST, Chemical and Engineering News, (1979), vol. 57, No. 21, p. 43.

W.J. Middleton, et al., a,a–Difluoroarylacetic Acids: Preparation from (Diethylamino)sulfur Trifluoride and x–Oxarylacetates, J. Org. Chem. (1980) 45,2883–2887.

* cited by examiner

*Primary Examiner*—Peter O'Sullivan
(74) *Attorney, Agent, or Firm*—Geoffrey L. Chase; Mary E. Bongiorno

(57) ABSTRACT

Diaryl-, dialkoxyalkyl-, alkylalkoxyalkyl-, arylalkoxyalkyl- and cyclic aminosulfur trifluorides fluorinating agents are disclosed.

13 Claims, No Drawings

THERMALLY STABLE AMINOSULFUR TRIFLUORIDES

CROSS-REFERENCE TO RELATED APPLICATIONS

The present application is a divisional application of U.S. Ser. No. 08/939,635 filed Sep. 29, 1997.

STATEMENT REGARDING FEDERALLY SPONSORED RESEARCH OR DEVELOPMENT

Not applicable.

BACKGROUND OF THE INVENTION

The development of safe, efficient, and simple methods for selective incorporation of fluorine into organic compounds has become a very important area of technology. This is due to the fact that fluorine strategically positioned at sites of synthetic drugs and agrochemical products significantly modifies and enhances their biological activities. The conversion of the C—O to the C—F bond, which is referred to herein a deoxofluorination, represents a viable method to produce selectively fluorinated organic compounds, but the low yields and hazards associated with the current deoxofluorination reagents and processes severely limit the application of this technique.

The introduction of fluorine into medicinal and agrochemical products can profoundly alter their biological properties. Fluorine mimics hydrogen with respect to steric requirements and contributes to an alteration of the electronic properties of the molecule. Increased lipophilicity and oxidative and thermal stabilities have been observed in such fluorine-containing compounds.

In view of the importance of organofluorine compounds, efforts aimed at the development of simple, safe, and efficient methods for their synthesis have escalated in recent years. The conversion of the carbon-oxygen to the carbon-fluorine bond by nucleophilic fluorinating sources (deoxofluorination) represents one such technique which has been widely used for the selective introduction of fluorine into organic compounds. A list of the deoxofluorination methods practiced to date includes: nucleophilic substitution via the fluoride anion; phenylsulfur trifluoride; fluoroalkylamines; sulfur tetrafluoride; $SeF_4$; $WF_6$; difluorophosphoranes and the dialkylaminosulfur trifluorides (DAST). The most common reagent of this class is diethylaminosulfur trifluoride, Et-DAST or simply DAST.

The DAST compounds have proven to be useful reagents for effecting deoxofluorinations. These reagents are conventionally prepared by reaction of N-silyl derivatives of 2° amines with $SF_4$. In contrast to $SF_4$, they are liquids which can be used at atmospheric pressure and at near ambient to relatively low temperature (room temperature or below) for most applications. Deoxofluorination of alcohols and ketones are particularly facile and reactions can be carried out in a variety of organic solvents (e.g., $CHCl_3$, $CFCl_3$, glyme, diglyme, $CH_2Cl_2$, hydrocarbons, etc.). Most fluorinations of alcohols are done at −78° C. to room temperature. Various functional groups are tolerated including CN, CONR2, COOR (where R is an alkyl group), and successful fluorinations have been accomplished with primary, secondary and tertiary (10, 2°, 3°) allylic and benzylic alcohols. The carbonyl to gem-difluoride transformation is usually carried out at room temperature or higher. Numerous structurally diverse aldehydes and ketones have been successfully fluorinated with DAST. These include acyclic, cyclic, and aromatic compounds. Elimination does occur to a certain extent when aldehydes and ketones are fluorinated and olefinic by-products are also observed in these instances.

While the DAST compounds have shown an versatility in effecting deoxofluorinations, there are several well recognized limitations associated with their use. The compounds can decompose violently and while adequate for laboratory synthesis, they are not practical for large scale industrial use. In some instances, undesirable by-products are formed during the fluorination process. Olefin elimination by-products have been observed in the fluorination of some alcohols. Often, acid-catalyzed decomposition products are obtained. The reagent's two step method used for their synthesis renders these relatively costly compositions only suitable for small scale syntheses.

The DAST reagents are recognized as fluorinating agents in U.S. Pat. Nos. 3,914,265 and 3,976,691. Additionally, Et-DAST and related compounds have been discussed in W. J. Middleton, New Fluorinating Reagents. Dialkylaminosulfur Fluorides, J. Org. Chem., Vol. 40, No. 5, (1975), pp 574–578. However, as reported by Messina, et al., Aminosulfur Trifluorides: Relative Thermal Stability, Journal of Fluorine Chemistry, 43, (1989), pp 137–143, these compounds can be problematic fluorinating agents due to their tendency to undergo catastrophic decomposition (explosion or detonation) on heating. Difficulties with major amounts of by-products in the fluorination reaction is also noted. See also M. Hudlicky, Fluorination with Diethylaminosulfur Trifluoride and Related Aminofluorosulfuranes, Organic Reaction, Vol. 35, (1988), pp 513–553.

Further, Russian Inventor's Certificate No. 433,136 published 15 December 1974 discloses sulfur dialkyl(alkylaryl) aminotrifluorides.

G. L. Hann, et. al., in Synthesis and Enantioselective Fluorodehydroxylation Reactions of (S)-2-(Methoxymethyl)pyrrolidin-1-ylsulphur Trifluoride, the First Homochiral Aminofluorosulphurane, J. Chem. Soc., Chem. Commun. (1989) pp 1650–1651, disclosed the aminosulfur trifluorides, (S)-2-(methoxymethyl)pyrrolidin-1-ylsulphur trifluoride and N-morpholinosulphur trifluoride as fluorinating agents for 2-(trimethylsiloxy)octane.

The compositions of the present invention overcome the drawbacks of the prior art fluorinating agents, including DAST, by providing more thermally stable fluorine bearing compounds which have effective fluorinating capability with far less potential of violent decomposition and attendant high gaseous by-product evolvement, as will be set forth in greater detail below.

BRIEF SUMMARY OF THE INVENTION

The present invention is an aminosulfur trifluoride composition having a structure with one or more:

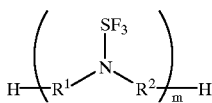

wherein m=1–5 and $R^1$ and $R^2$ are:
 (1) when m=1, individually aryl or meta- or para-substituted aryl radicals in which the meta- or para-substitution is selected from the group consisting of normal and branched $C_{1\text{-}10}$, trifluoromethyl, alkoxy, aryl $C_{6\text{-}10}$, nitro, sulfonic ester, N,N-dialkylamino and halogens; or
 (2) when m=1, individually aryl radicals which are fused or linked to one another; or
 (3) when m=1, one of $R^1$ and $R^2$ is an aryl radical and the other is an at least 5 member saturated cyclic hydrocarbon radical having zero to three heteroatoms selected from the group consisting of oxygen, nitrogen and mixtures thereof; or
 (4) when m=1, one of $R^1$ and $R^2$ is an aryl radical and the other is an at least 5 member saturated cyclic hydrocarbon radical having zero to three heteroatoms selected from the group consisting of oxygen, nitrogen and mixtures thereof wherein said cyclic hydrocarbon radical is fused to said aryl radical; or
 (5) when m=1, together a cyclic ring having 2 to 10 carbon ring members and 1 heteroatom selected from the group consisting of oxygen, nitrogen and alkylated nitrogen wherein said ring has 1 to 2 alkoxyalkyl functionalities; or
 (6) when m=1, together an unsaturated cyclic ring having 2 to 4 carbon ring members and one to three heteroatoms selected from the group consisting of oxygen, nitrogen, protonated nitrogen and alkylated nitrogen wherein said ring has one to three functional groups selected from hydrogen, normal and branched $C_{1\text{-}10}$ alkyl, haloalkyl, alkoxy, aryl halogen, cyano, nitro and amino; or
 (7) when m=1, individually alkoxyalkyl radicals; or
 (8) one of $R^1$ and $R^2$ are alkoxyalkyl and the other is selected from the group consisting of alkyl and aryl radicals; or
 (9) when m=2–5, $R^1$ is a single phenyl radical linked to each —$NSF_3$ radical and $R^2$ is an aryl radical having $C_6$ to $C_{10}$; or
 (10) when m=2–5, $R^1$ and $R^2$ are individually divalent aryl radicals of $C_6$ to $C_{10}$ linked to adjacent —$NSF_3$ radicals except $R^1$ and $R^2$ are monovalent aryl radicals having $C_6$ to $C_{10}$ where $R^1$ and $R^2$ are linked to only one —$NSF_3$ radical.

Preferably, $R^1$ and $R^2$ are:
 (1) individually aryl and para-substituted aryl radicals in which the para-substitution is selected from the group consisting of normal and branched $C_{1\text{-}10}$ alkyl, trifluoromethyl, alkoxy, aryl $C_{6\text{-}10}$, nitro, sulfonic ester, N,N-dialkylamino and halogens; or
 (2) individually alkoxyalkyl radicals; or
 (3) one of $R^1$ and $R^2$ are alkoxyalkyl and the other is selected from the group consisting of alkyl and aryl radicals.

Preferably, the alkoxyalkyl radical has a carbon content of 2–10 in a normal or branched structure with at least one O atom or a polyether chain, —$(R^1\text{—}O)_n$—R where n=1–10, $R=C_{1\text{-}10}$ normal or branched alkyl, $R^1=C_{2\text{-}3}$ normal or branched alkyl.

Preferably, the aryl radical is selected from the group consisting of a six carbon membered aromatic ring, a ten carbon membered aromatic fused ring and mixtures thereof.

Preferably, the meta- or para-substituted aryl radical is substituted with a group selected from the group consisting of an alkyl radical of $C_1$ to $C_{10}$ in a normal or branched structure, an alkoxy radical of $C_1$ to $C_{10}$ in a normal or branched structure, halogens, trifluoromethyl and mixtures thereof.

More preferably, the aryl radical of the meta- or para-substituted aryl radical is selected from the group consisting of a six carbon membered aromatic ring, a ten carbon membered aromatic fused ring and mixtures thereof.

More preferably, the composition has the general structure:

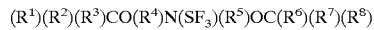

$(R^1)(R^2)(R^3)CO(R^4)N(SF_3)(R^5)OC(R^6)(R^7)(R^8)$ wherein $R^{1\text{-}3,\ 6\text{-}8}$ are individually H, normal or branched alkyl $C_{\text{-}10}$ or aryl $C_{6\text{-}10}$ and $R^{4\text{-}5}$ are $C_{2\text{-}10}$ normal or branched alkyl.

More preferably, the composition has the general structure:

$R^3OR^4N(SF_3)R^5OR^6$ wherein $R^3$ and $R^6$ are individually $C_1$ to $C_{10}$ in a normal or branched chain alkyl and $R^4$ and $R^5$ are $C_{2\text{-}10}$ normal or branched alkyl.

Most preferably, the composition has the specific structure:

$CH_3OCH_2CH_2N(SF_3)CH_2CH_2OCH_3$

An alternative preferred embodiment has the composition having the general structure:

$R^7N(SF_3)R^8OR^9$ wherein $R^7$ and $R^9$ are individually $C_1$ to $C_{10}$ normal or branched alkyl and $R^8$ is $C_2$ to $C_{10}$ normal or branched alkyl.

Another alternative preferred embodiment has the composition having the general structure:

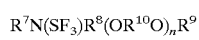

$R^7N(SF_3)R^8(OR^{10}O)_nR^9$ wherein $R^7$and $R^9$ are individually $C_1$ to $C_{10}$ normal or branched alkyl, $R^1$ is $C_2$ to $C_{10}$ normal or branched alkyl, $R^{10}=C_{2\text{-}3}$ alkyl and n=5.

A more preferred embodiment of the alternative composition has the specific structure:

$CH_3N(SF_3)CH_2CH_2OCH_3$

In yet another alternative preferred embodiment the composition has the structure:

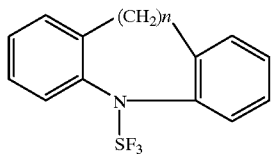

where n=2–6.

In a third alternative preferred embodiment the composition has the structure:

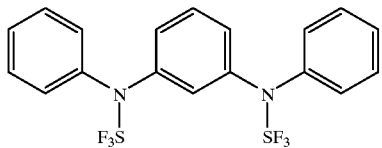

In a fourth alternative preferred embodiment the composition has the structure:

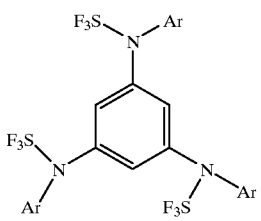

where Ar is an aryl radical of $C_6$ to $C_{10}$.

In a fifth alternative preferred embodiment the composition has the structure:

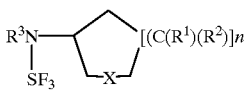

wherein $R^3$ is an aryl radical of $C_6$ to $C_{10}$ n=1–5, $R^1$ and $R^2$ are individually H or alkyl $C_{1-10}$ and X=zero to three ring element substitutions of O or $NR^4$ where $R^4$=H, normal or branched alkyl $C_{1-10}$.

In a sixth alternative preferred embodiment the composition has the structure:

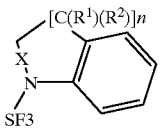

wherein $R^1$ and $R^2$=individually H or normal or branched alkyl $C_{1-10}$, n=1–5 and X=zero to three ring element substitutions of O or $NR^3$ where $R^3$=H, normal or branched alkyl $C_{1-10}$.

In a seventh alternative preferred embodiment the composition has the structure:

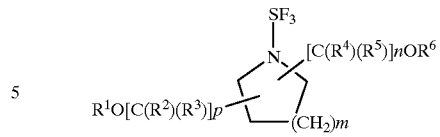

wherein $R^1$ and $R^6$ are individually normal or branched alkyl $C_{1-10}$, $R^{2-5}$, are individually H, or normal or branched alkyl $C_{1-10}$, m=1–10, n=1–10, and p=1–10.

In an eighth alternative preferred embodiment the composition has the structure:

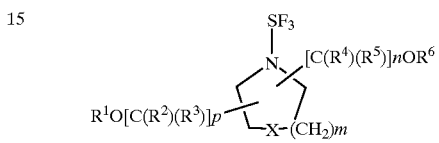

wherein $R^1$ and $R^6$ are individually normal or branched alkyl $C_{1-10}$, $R^{2-5}$, are individually H, or normal or branched alkyl $C_{1-10}$, m=1–10, n=1–10, and p=1–10, and X=a ring element substitution of O or $NR^7$ where $R^7$=H, normal or branched alkyl $C_{1-10}$.

In a ninth alternative preferred embodiment the composition has the structure:

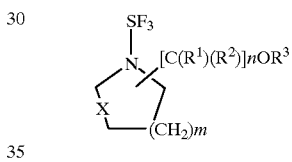

where m=1–10, n=1–10, $R^1$ and $R^2$=individually H, or normal or branched alkyl $C_{1-10}$, $R^3$=normal or branched alkyl $C_{1-10}$ and X=a ring element substitution of O, $NR^4$ where $R^4$=normal or branched alkyl $C_{1-10}$.

BRIEF DESCRIPTION OF THE SEVERAL VIEWS OF THE DRAWINGS

Not Applicable

DETAILED DESCRIPTION OF THE INVENTION

Several novel aminosulfur trifluorides are presented in this invention. These compounds have been shown to be very useful for effecting deoxofluorination of alcohols and ketones. In addition, thermal analysis studies indicate that they should be much safer to use than the currently available dialkylaminosulfur trifluorides (DAST).

The simplicity of the method used for preparing the new aminosulfur trifluorides, as described hereafter, combined with their relative safety in use should make these compounds attractive for large scale production.

These compounds are identified as follows by general class: The compositions fall into the following two classes: Diaryl systems and alkoxyalkyl aminosulfur trifluorides.

1. Diaryl Systems

$ArN(SF_3)Ar'$ where Ar and Ar' are the same or different aryl groups (i.e., mixed compounds). The aryl groups can be mono or polynuclear, the latter encompassing isolated ring or fused-ring groups and each contemplates substituted aryl groups.

For example, when both groups are derived from benzene, the general formula is

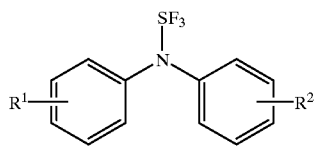

a) $R^1$ and $R^2$ represent one or more substituents (like or different). Examples provided (Table 1) for $R^1$, $R^2$=H, p-Cl, p-OCH$_3$, p-CH$_3$. These groups may be para or meta to the NSF$_3$ group. $R^1$, $R^2$ can additionally be OR (R=alkyl or aryl), Br; I, F, alkyl or aryl groups, CF$_3$, NO$_2$, SO$_3$R (R=alkyl or aryl), NR$_2$ (R=alkyl or aryl). These groups may be ortho, meta or para to the NSF$_3$ group.

b) Aryl naphthyl systems (Table 1)

c) Fused or linked diaryl systems, e.g.,

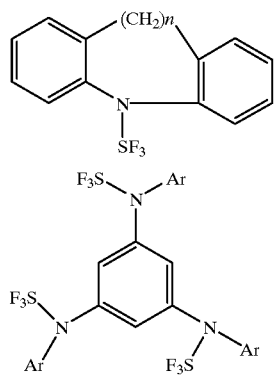

n=2 or more

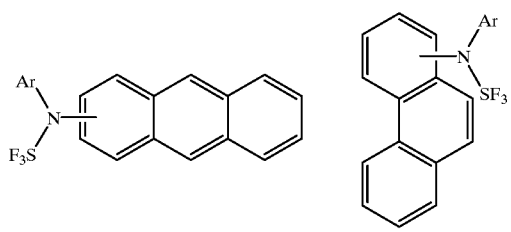

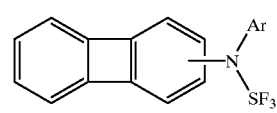

Furthermore, oligomeric or polymeric analogues may be used in which aromatic units are linked via the nitrogen of the NSF$_3$ group, such as:

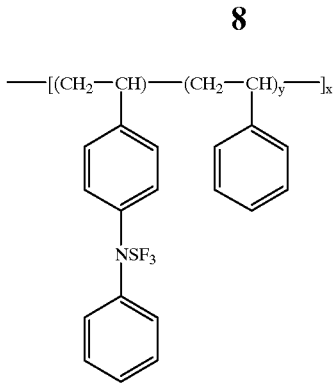

where y = 0–6 and x = 1–1000

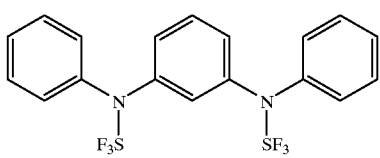

d) Heteroatom (O,N) containing aromatic systems (branched or fused)

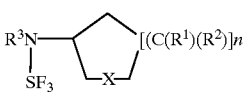

wherein $R^3$ is an aryl radical of C$_6$ to C$_{10}$, n=1–5, $R^1$ and $R^2$ are individually H or alkyl C$_{1-10}$ and X=zero to three ring element substitutions at any available position on the ring of O or NR$^1$ where $R^4$=H, normal or branched alkyl C$_{1-10}$.

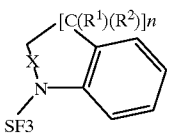

wherein $R^1$ and $R^2$=individually H or normal or branched alkyl C$_{1-10}$. n=1–5 and X=zero to three ring element substitutions at any available position on the ring of O or NR$^3$ where $R^3$=H. normal or branched alkyl C$_{1-10}$.

One of the aromatic ring system attached to the N—SF$_3$ group may be 5-membered or greater and contain heteroatoms such as O(1–3) or N(1–3). The heteroatom-containing ring may be branched from the N—SF$_3$ group or fused to the other aromatic ring (Ar).

2. Alkoxyalkylamine Systems a)

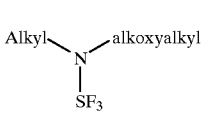

Table 5 b)

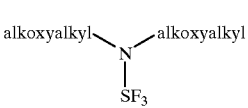

Table 5 c)

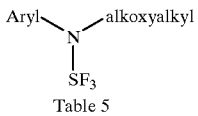

Table 5

Alkyl=normal or branched $C_{1-10}$. Alkoxyalkyl=(a) —$R^1$—O—$R^2$, where $R^1$ is $C_{2-10}$ normal or branched alkyl and $R^2$ is $C_{1-10}$ normal or branched alkyl or (b) —$(R^3$—O$)_n$—$R^2$, where $R^2$ is $C_{1-10}$ normal or branched alkyl and $R^3$ is $C_{2-3}$ normal or branched alkyl and n=1–10.

d) Alkoxyalkyl branched from ring systems containing $NSF_3$

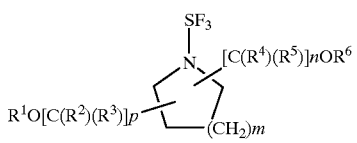

wherein $R^1$ and $R^6$ are individually normal or branched alkyl $C_{1-10}$, $R^{2-5}$, are individually H or normal or branched alkyl $C_{1-10}$, m=1–10, n=1–10, and p=1–10.

e) Alkoxyalkyl branched heteroatom ring systems containing $NSF_3$

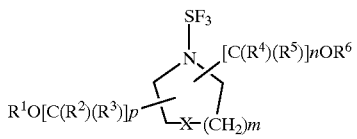

wherein $R^1$ and R6 are individually normal or branched alkyl $C_{1-10}$, $R^{2-5}$, are individually H, or normal or branched alkyl $C_{1-10}$, m=1–10, n=1–10, and p=1–10, and X=a ring element substitution at any available position of the ring of O or $NR^7$ where $R^1$=H, normal or branched alkyl $C_{1-10}$.

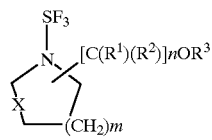

where m=1–10, n=1–10, $R^1$ and $R^2$=individually H, or normal or branched alkyl $C_{110}$, $R^3$=normal or branched alkyl $C_{1-10}$ and X=a ring element substitution at any available position of the ring of O, $NR^4$ where $R^4$=normal or branched alkyl $C_{1-10}$.

A preferred class of deoxofluorination reagents has the general structure:

$(R^1)(R^2)(R^3)CO(R^4)N(SF_3)(R^5)OC(R^6)(R^7)(R^8)$ wherein $R^{1-3,\ 6-8}$ are individually H, normal or branched alkyl $C_{1-10}$ or aryl $C_{6-10}$ and $R^{4-5}$ are normal or branched $C_{2-10}$. A more specific class of preferred deoxofluorination reagents has the general structure:

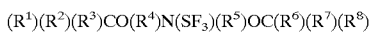

wherein $R^3$ and $R^6$ are individually $C_1$ to $C_{10}$ normal or branched chain, $R^{4-5}$ are $C_{2-10}$ normal or branched alkyl.

More specifically the deoxofluorination reagent has the specific structure:

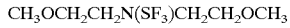

For the purpose of this invention the following definitions are provided. Alkyl shall mean normal and branched carbon radicals up to ten carbons. Aryl shall mean six and ten member-carbon rings having aromatic character. Fused aryl shall mean aromatic rings containing two common carbon atoms. Linked aryl shall mean aromatic rings joined together by a bond from a carbon atom of one ring to a carbon atom of another ring. Heteroatoms shall mean oxygen and/or nitrogen in a carbon membered radical. Para-substitution on an aryl ring shall include H, p-Cl, p-$OCH_3$, p-$CH_3$, OR (R=alkyl $C_{1-10}$ or aryl C6-10), Br, I, F, alkyl $C_{1-10}$ or aryl $C_{10}$ groups, $NO_2$, $SO_3R$ (R=H, alkyl $C_{1-10}$ or aryl C6-10), $NR_2$ (R=H, alkyl $C_{1-10}$ or aryl $C_{6-10}$). Alkoxyalkyl typically means an oxygen bridging two alkyl groups, but it is also contemplated to include polyethers, such as: —O(—RO)$_n$R' where R and R' are $C_{1-3}$ alkyl and n=1–10.

To develop thermally stable aminosulfur trifluorides, the inventors considered compounds which would not produce gaseous by-products on decomposition. The production of HF via abstraction of acidic protons in the vicinity of the N—$SF_3$ group by fluorine ion is believed to be one factor which contributes to the instability of the dialkylaminosulfur trifluorides. Consequently, compounds lacking such protons are attractive candidates for the present invention, although compounds with such protons can be useful. In order to circumvent the thermal instability which results from molecular disproportionation of dialkylaminosulfur trifluoride, the inventors prepared compounds which possess sterically demanding groups attached to the N—$SF_3$ function. Aminosulfur trifluorides with a highly electron deficient nitrogen bonded to the $SF_3$ group are also appropriate since molecular disproportionation will be less significant in these compounds.

The diaryl, arylalkyl and alkoxyalkylaminosulfur trifluorides fulfill most of the structural requirements for a thermally stable product. The preparation and reactions of these compounds are described below.

An attempted synthesis of diphenylaminosulfur trifluoride by the conventional reaction route of the N-trimethylsilyl derivative of diphenylamine with $SF_4$ proved to be difficult. Only a small amount of product (<10% yield) was obtained in a reaction carried out at room temperature.

A synthetic route to dialkyl and arylalkylaminosulfur trifluorides described in Russian Inventor's Certificate No. 433,136 was used in which a secondary (2°) amine is reacted with $SF_4$ in ethyl ether containing triethylamine for the preparation of several novel diarylaminosulfur trifluorides. This simple one-step process (as opposed to the two-step method via a silyl amine) afforded a virtual quantitative yield of products at temperatures ranging from −10° C. to room temperature. Table 1 summarizes the diaryl compounds which were prepared by this method. The procedure proved to be particularly useful for the preparation of diarylaminosulfur trifluorides bearing both electron withdrawing and electron donating groups at the para position of the aromatic rings. The sterically hindered N-phenyl-N-naphthyl-amine was successfully converted to the diarylaminosulfur trifluoride at room temperature. However, the preparation of diarylaminosulfur trifluorides bearing substituent groups at the ortho position of the aromatic ring proved to be more difficult. None of the desired products were obtained in reactions carried out at −10° C. or room temperature with either 2,2'-dimethyl-diphenylamine or 2,2'-dimethoxy-diphenylamine. Instead only starting material was recovered after several hours (3–24 h) of reaction time. The steric hindrance imposed by the adjacent substituent groups on the aromatic ring seems to be significant in these compounds.

The aminosulfur trifluoride is synthesized by reaction of a secondary amine with $SF_4$ in a non-aqueous solvent that will not react chemically with $SF_4$ or the aminosulfur trifluoride product. Examples include ethers, e.g., ethylether ($Et_2O$), tetrahydrofuran (THF), halogenated hydrocarbons, e.g., $CH_2Cl_2$, freons, hydrocarbons, e.g., toluene, hexane, tertiary amines, liquid $SO_2$ and supercritical $CO_2$.

The reaction can be carried out at temperatures ranging from −90° C. or the freezing point of the solvent to the boiling point of the solvent.

The reaction mixture may be homogenous or heterogenous.

The secondary amine is represented by $R^1R^2NH$. $R^1$=alkyl (cyclic or non-cyclic, with or without heteroatoms), aryl, or alkoxyalkyl. $R^2$=alkyl (cyclic or non-cyclic, with or without heteroatoms), aryl or alkoxyalkyl. $R^1$ may or may not be the same as $R^2$.

The tertiary amine is represented by $R^1R^2R^3N$. $R^1$, $R^2$ or $R^3$=alkyl (cyclic or non-cyclic, with or without heteroatoms), or aryl. This includes tertiary amines which contain the N-atom in a ring, e.g., N-methylpiperidine or in a chain, e.g., triethylamine. It also includes tertiary amines which contain the N-atom at a bridge-head, e.g., quinuclidine or triethylene diamine and in fused rings, e.g., diazabicycloundecane (DBU). Compounds containing >1, tertiary amine group in the molecule can also be used. The tertiary amine could also function as the reaction solvent. Examples of specific amines employed for the synthesis of $R_2NSF_3$ reagents should also be effective for the in situ process described below.

No aminosulfur trifluoride product was obtained when pyridine or 3-methylpyridine was used instead of a tertiary amine; however, more basic pyridines than the latter are expected to be useful.

No aminosulfur trifluoride product was obtained when NaF or CsF was used instead of a tertiary amine. Thus, its utilization in the process beyond simply acting as an HF acceptor is an essential feature of the invention.

The substrate for fluorination may be an alcohol, an aldehyde, ketone, carboxylic acid, aryl or alkyl sulfonic acid, aryl or alkyl phosphonic acid, acid chlorides, silyl chlorides, silyl ethers, sulfides, sulfoxides, epoxides, phosphines and thiophosphines.

Water or a low molecular weight alcohol ($CH_3OH$, $C_2H_5OH$, etc.) may be added to hydrolyze the intermediate sulfinyl fluoride for disposal and to generate the starting secondary amine.

The fluorinated product may be separated from the aqueous acidic mixture by extraction into a water immiscible organic solvent.

The desired product may be distilled and thus isolated from the crude reaction mixture.

Aminosulfur trifluorides derived from relatively electron deficient diarylamines were found to be unstable. In an attempted preparation of 4,4'-dichloro-diphenyl aminosulfur trifluoride, the amine was reacted with $SF_4$ in ethyl ether/triethylamine ($Et_2O$/TEA) at 0° C. After work-up a light yellow solid was isolated. This solid product darkened considerably on standing at room temperature (<1 h) forming 4-chlorophenyl iminosulfur difluoride as the principal decomposition product.

TABLE 1

Preparation of Diarylaminosulfur trifluorides from $SF_4$ and Diarylamines

| Starting Material | Reaction Conditions | Product (Yield) |
|---|---|---|
| 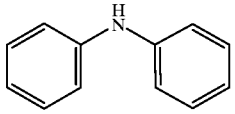<br>1 | $SF_4$, $Et_2O$, or THF, TEA<br>−10° C., 3 h | 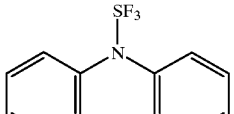<br>2 (quantitative) |
| 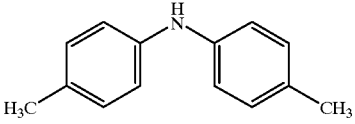<br>3 | $Et_2O$, or THF<br>−10° C., 3 h | 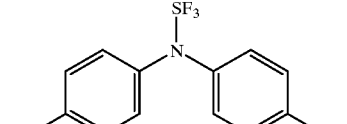<br>4 (quantitative) |

TABLE 1-continued

Preparation of Diarylaminosulfur trifluorides from $SF_4$ and Diarylamines

| Starting Material | Reaction Conditions | Product (Yield) |
|---|---|---|
| 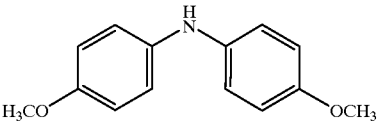 5 | $Et_2O$, or THF −10° C., 3 h | 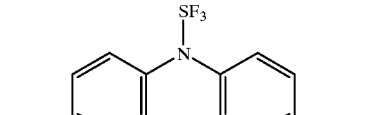 6 (quantitative) |
| 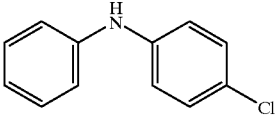 7 | $Et_2O$, or THF −10° C., 3 h | 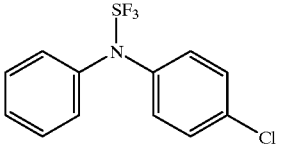 8 (quantitative) |
| 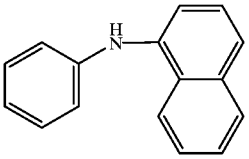 9 | $Et_2O$, or THF −10° C., 3 h | 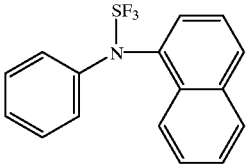 10 (quantitative) |
| 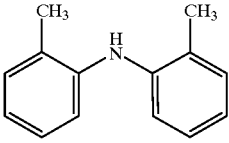 11 | THF −78°-RT, 3 h | Starting material |
| 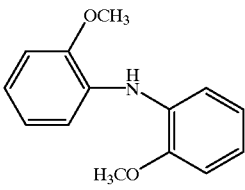 12 | $Et_2O$, −78°-RT, 3 h | Starting material |
| 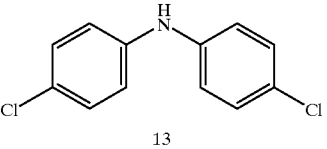 13 | $Et_2O$, −78°-RT, 3 h | 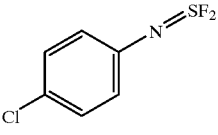 14 |

The fused diarylamines were found to be less reactive towards $SF_4$ than the freely rotating diarylamines. This is possibly due to their more rigid nature and hence increased steric hindrance. These compounds react with $SF_4$ at room temperature in tetrahydrofuranltriethylamine (THF/TEA), but do not produce the corresponding aminosulfur trifluoride. Instead, the major products were the iminosulfur difluorides 16, 18, 20, 23 (Table 2) obtained by elimination of fluoride from the N—$SF_3$ group and nucleophilic displacement of the thioiminium ion.

TABLE 2

Reaction of SF$_4$ with fused-ring diaryl compounds

| Starting material | Reaction conditions | Product |
|---|---|---|
| 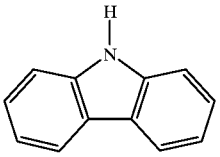<br>15 | SF$_4$, THF,<br>−78° C.-RT, 3 h | 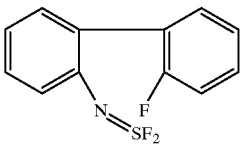<br>16 |
| 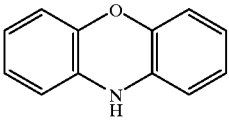<br>17 | SF$_4$, THF,<br>−78° C.-RT, 3 h | 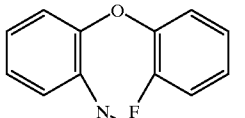<br>18 |
| 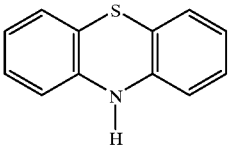<br>19 | SF$_4$, THF,<br>−78° C.-RT, 3 h | 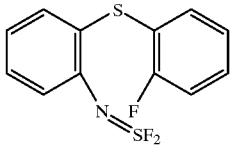<br>20 |
| 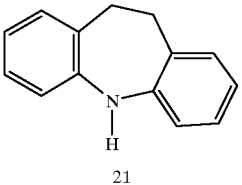<br>21 | SF$_4$, THF,<br>−78° C.-RT, 3 h | 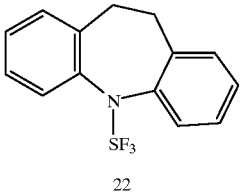<br>22<br>+<br>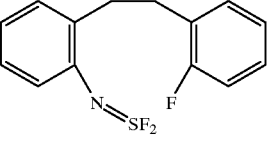<br>23 |

Aromatic heterocyclic amines such as indole and 2-methylindole were perceived as good candidates for the synthesis of stable aminosulfur trifluorides since they lack acidic α-hydrogens. However, on reaction of these compounds with SF$_4$ in Et$_2$O/TEA at —10° C. only viscous tarry products were obtained (Table 3). An examination of the $^1$H and $^{19}$F NMR spectra of these products shows that the N—SF$_3$ compounds were not formed. The saturated indoles (26, 28, Table 3), however, afford good yields of the corresponding aminosulfur trifluorides on reaction with SF$_4$ in Et$_2$O/TEA at −78° C. These compounds which appeared to be stable on initial preparation decomposed rapidly on storage (<3 days).

TABLE 3

Reaction of SF$_4$ with heterocyclic amines in Et$_2$O/TEA

| Starting material | Reaction Conditions | Product (yield) |
|---|---|---|
| 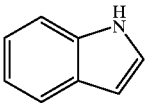<br>24 (indole) | SF$_4$, Et$_2$O, TEA<br>−78° C. to −10° C. | Tarry reaction product,<br>No SF$_3$ derivative |
| 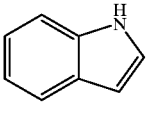<br>25 (2-methylindole) | SF$_4$, Et$_2$O, TEA<br>−78° C. to −10° C. | Tarry reaction product,<br>No SF$_3$ derivative |
| 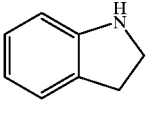<br>26 (indoline) | SF$_4$, Et$_2$O, TEA<br>−78° C. to −10° C. | 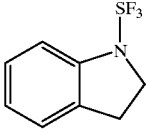<br>27<br>quantitative |
| 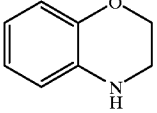<br>28 | SF$_4$, Et$_2$O, TEA<br>−78° C. to −10° C. | 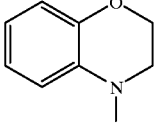<br>29<br>quantitative |

Russian Inventor's Certificate No. 433,136 reported the preparation of N-ethyl-N-phenylaminosulfur trifluoride in 78% yield by reaction of N-ethyl-N-phenylamine with SF$_4$ in Et$_2$O containing tertiary (3°) amines. The present inventors confirmed these results and extended the method to the preparation of the N-methyl analog (Table 4). The arylalkyl amines were much more reactive towards SF$_4$ than the diarylamines and the reactions were completed at −78° C. with quantitative formation of products.

TABLE 4

Preparation of arylalkyl aminosulfur trifluorides

| Starting material | Reaction conditions | Product (yield) |
|---|---|---|
| 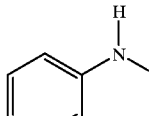<br>30 | SF$_4$, Et$_2$O, TEA<br>−78° C. 1 h | 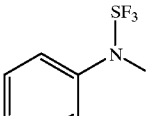<br>31<br>quantitative |
| 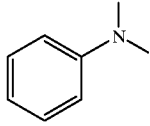<br>32 | SF$_4$, Et$_2$O, TEA<br>−78° C. 1 h | 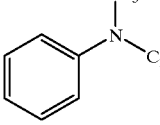<br>33<br>quantitative |

The inventors have further determined that dialkylaminosulfur trifluorides that contain an oxygen atom in the vicinity of the SF$_3$ group possess enhanced thermal stability. The aminosulfur trifluorides with the highest reported decomposition temperatures are N-morpholinosulfur trifluoride and (S)-2-(methoxyethyl) pyrrolidin-1-yl-sulfur trifluoride. The increased thermal stability of these compounds may result from coordination of the electron-rich oxygen atom with sulfur affording a conformationally rigid structure. However, the inventors found that (S)-2-(methoxyethyl) pyrrolidi n-1-yl-sulfur trifluoride was a poor fluorinating reagent for deoxofluorination of cyclooctanol, as reported below.

The preparation of aminosulfur trifluorides by reaction of the amine with SF$_4$ in Et$_2$O/TEA was successfully applied to the preparation of several alkoxyalkylaminosulfur trifluorides (Table 5). These include compounds bearing one or two methoxy groups. The reactions of the precursor amines with SF$_4$ were quite rapid at −78° C. affording high yields of products.

TABLE 5

Preparation of alkoxyalkyl aminosulfur trifluorides

| Starting material | Reaction conditions | Product (Yield) |
|---|---|---|
| 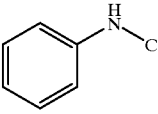<br>34 | SF$_4$, Et$_2$O, TEA<br>−78° C., 1 h | 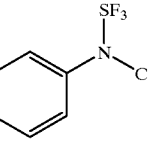<br>35<br>quantitative |
| CH$_3$NHCH$_2$CH$_2$OMe<br>36 | SF$_4$, Et$_2$O, TEA<br>−78° C., 1 h | CH$_3$N(SF$_3$)CH$_2$CH$_2$OMe<br>37 |

TABLE 5-continued

Preparation of alkoxyalkyl aminosulfur trifluorides

| Starting material | Reaction conditions | Product (Yield) |
|---|---|---|
|  |  | quantitative |
| 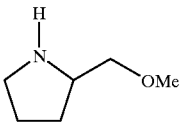<br>38 | $SF_4$, $Et_2O$, TEA<br>−78° C., 1 h | 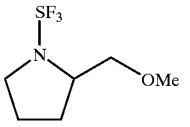<br>39<br>quantitative |
| $MeOCH_2CH_2NHCH_2CH_2OMe$<br>40 | $SF_4$, $Et_2O$, TEA<br>−78° C., 1 h | $MeOCH_2CH_2N(SF_3)CH_2CH_2OMe$<br>41<br>quantitative |

In order to study the effect of N-atom coordination on product stability and reactivity of aminosulfur trifluorides, the inventors explored the synthesis of compounds containing a 3° amine group in proximity to the N—$SF_3$ functionality. A reaction of $SF_4$ with N,N,N',N'-tetraethyl diethylene triamine in $Et_2O$ at −10° C. afforded no aminosulfur trifluoride product, but a compound with a C—F bond (possibly $CH_3CHFNHCH_2CH_3NEt_2$) was discernible on examination of the $^{19}F$ NMR of the reaction mixture. This seems to indicate an elimination of the 3° amine group with addition of HF to the resulting olefinic intermediate. However, the reaction of $SF_4$ with N,N',N'-trimethylethylene diamine in $Et_2O$/TEA at −10° C. followed a completely different path producing an iminosulfur difluoride salt (43, Table 6) instead of the desired aminosulfur trifluoride. A similar product (47, Table 6) was obtained from N-phenyl substituted diamine on reaction with $SF_4$.

On reaction of the silyl derivative of N,N',N'-trimethylethylene diamine with $SF_4$ in $Et_2O$, the predominant product was the iminosulfur difluoride salt as obtained from the free amine. A reaction of the amine carried out in the presence of a proton sponge as base instead of triethylamine afforded a product containing a C—F bond ($CH_3NHCHFCH_3$) resulting from elimination of the 3° amine and addition of HF.

TABLE 6

Reaction of 3° amino substituted dialkylamines with $SF_4$

| Starting material | Reaction conditions | Product |
|---|---|---|
| $CH_3NHCH_2CH_2N(CH_3)_2$<br>42 | $SF_4$, $Et_2O$/TEA<br>−78° C. to RT, 3 h | $H_3C-\overset{+}{\underset{\underset{SF_2}{\parallel}}{N}}-CH_2CH_2N(CH_3)_2$ $HF_2^-$<br>43 |
| $(Et)_2NCH_2CH_2NHCH_2CH_2N(Et)_2$<br>44 | $SF_4$, $Et_2O$/TEA<br>−78° C. to RT, 3 h | $CH_3CHFNHCH_2CH_2N(Et)_2$<br>45 |
| $PhNHCH_2CH_2N(CH_3)_2$<br>46 | $SF_4$, $Et_2O$/TEA<br>−78° C. to RT, 3 h | $Ph-\overset{+}{\underset{\underset{SF_2}{\parallel}}{N}}-CH_2CH_2N(CH_3)_2$ $HF_2^-$<br>47 |

To further demonstrate that aminosulfur trifluorides lacking α-hydrogens which cannot readily produce HF should be more thermally stable, the inventors performed the preparation of $SF_3$ derivatives of an arylsulfonamide, an arylsulfonimide, an imide, and a carbamate.

The reaction of $SF_4$ with these compounds at room temperature afforded none of the desired products. Instead, the iminosulfur difluorides 49, 51, 54 (Table 7) were obtained as the principal products. The highly electron-deficient nature of the nitrogen atom of these precursor trifluorides might be responsible for the products observed.

TABLE 7

Reaction of $SF_4$ with aryl sulfonamide, aryl sulfonamide imide and carbamate

| Starting material | Reaction conditions | Product |
|---|---|---|
| $PhSO_2NHSO_2Ph$<br>48 | $SF_4$, THF/TEA<br>−78° C. to RT,<br>3 h | $PhSO_2-N=SF_2$<br>49 |

TABLE 7-continued

Reaction of SF$_4$ with aryl sulfonamide,
aryl sulfonamide imide and carbamate

| Starting material | Reaction conditions | Product |
|---|---|---|
| PhSO$_2$NHPh  50 | SF$_4$, THF/TEA −78° C. to RT, 3 h | Ph—N=SF$_2$  51 |
| PhNHCOOEt  52 | SF$_4$, THF/TEA −78° C. to RT, 3 h | Ph—N=SF$_2$  51 |
| (succinimide) 53 | SF$_4$, THF/TEA −78° C. to RT, 3 h | 54 |

Deoxofluorination of cyclooctanol with diarylaminosulfur trifluorides proceeds rapidly at −78° C. in CH$_2$Cl$_2$ to produce cyclooctylfluoride and cyclooctene with the former predominating (Table 8). Differing ratios of fluoride to olefin were observed with the various aromatic substituted trifluorides. The sterically hindered N-naphthyl-N-phenylaminosulfur trifluoride reacted quite slowly affording only a 10% conversion of starting material to products after 16 h at room temperature. A rapid conversion to the monofluoride was obtained with N-methyl-N-phenylaminosulfur trifluoride. Among the alkoxyalkyl compounds 35–41 (Table 5), the phenyl substituted aminosulfur trifluoride (35) proved to be the most reactive affording fluorination at −78° C. in 1 h as compared to the methyl and bisalkoxyalkyl compounds (37, 41, respectively) which required longer reaction times (~3 hr) at −78° C. to effect the same conversion.

TABLE 8

Deoxofluorination of cyclooctanol

| Aminosulfur trifluoride | Reaction conditions | Ratio of cyclooctyl fluoride/ cyclooctene |
|---|---|---|
| (Ph)$_2$NSF$_3$  2 | CH$_2$Cl$_2$, −78° C. 1 h | 70:30 |
| (4-MeC$_6$H$_4$)$_2$NSF$_3$  4 | CH$_2$Cl$_2$, −78° C. 1 h | 90:10 |
| (4-MeOC$_6$H$_4$)$_2$NSF$_3$  6 | CH$_2$Cl$_2$, −78° C. 1 h | 76:24 |

TABLE 8-continued
Deoxofluorination of cyclooctanol
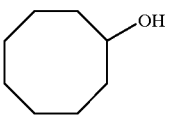
| Aminosulfur trifluoride | Reaction conditions | Ratio of cyclooctyl fluoride/cycloctene |
|---|---|---|
| 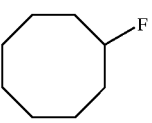 8 | CH$_2$Cl$_2$, −78° C. 1 h | 94:6 |
| 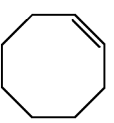 10 | CH$_2$Cl$_2$, RT 16 h, 10% conversion | |
| 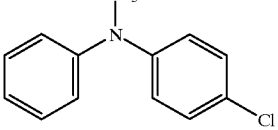 31 | CH$_2$Cl$_2$, −78° C. 1 h | 99:1 |
| 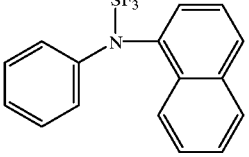 35 | CH$_2$Cl$_2$, −78° C. 1 h | 90:10 |
| CH$_3$N(SF$_3$)CH$_2$CH$_2$OMe 37 | CH$_2$Cl$_2$, −78° C. 3 h | 85:15 |
| MeOCH$_2$CH$_2$N(SF$_3$)CH$_2$CH$_2$OMe 41 | CH$_2$Cl$_2$, −78° C. 3 h | 85:15 |
| 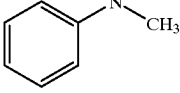 39 | CH$_2$Cl$_2$, −78° C. 8 h | 17/6 |

In contrast to the superior deoxofluorination of cyclooctanol for the reagents reported in Table 8, (S)-2-(methoxyethyl) pyrrolidin-1-yl-sulfur trifluoride was a poor deoxofluorination reagent for cyclooctanol. In a reaction carried out at −78° C. in $CH_2Cl_2$ for 8 h only 17% cyclooctyl fluoride was produced and 6% cyclooctene, as determined by nuclear magnetic resonance.

Table 9 summarizes the results obtained on fluorination of 4-t-butyl cyclohexanone with the aminosulfur trifluorides. All of the compounds examined except N-naphthyl-N-phenylaminosulfur trifluoride converted the ketone to a mixture of 4-t-butyl-difluorocyclohexane and 4-t-butyl-1-fluorocyclohexene, with the former predominating. The fluorination of this ketone was much slower than observed for the fluorination of cyclooctanol. A complete conversion to the fluorinated products required several days at room temperature in $CH_2Cl_2$. However, addition of a catalytic amount of HF (generated in-situ from EtOH) accelerated the rate of reaction considerably. The reaction time was reduced from several days to 16 h when the diaryl, arylalkyl, and N-methoxyethyl-N-phenylaminosulfur trifluorides were reacted with 4-t-butylcyclohexanone in the presence of HF. The effect of HF on reaction rate was, however, less pronounced with the alkoxyalkyl aminosulfur trifluorides 37 and 41. A reasonable reaction time (40 h) for complete fluorination of the ketone with bis(methoxyethyl-aminosulfur trifluoride (41) was obtained when the reaction was carried out at 40° C.

TABLE 9

Deoxofluorination of 4-t-butylcyclohexanone

| Aminosulfur trifluoride | Reaction conditions | Ratio of difluoride/vinyl fluoride |
|---|---|---|
| 2 (diphenylaminosulfur trifluoride) | $CH_2Cl_2$, RT, 5 days | 96:4 |
| 4 (bis(4-methylphenyl)aminosulfur trifluoride) | $CH_2Cl_2$, RT, EtOH(0.2 eq), 16 h | 88:12 |
| 6 (bis(4-methoxyphenyl)aminosulfur trifluoride) | $CH_2Cl_2$, RT, EtOH(0.2 eq), 16 h | 82:18 |

TABLE 9-continued

Deoxofluorination of 4-t-butylcyclohexanone

| Aminosulfur trifluoride | Reaction conditions | Ratio of difluoride/vinyl fluoride |
|---|---|---|
| Compound 8: PhN(SF₃)(4-ClC₆H₄) | CH₂Cl₂, RT, EtOH(0.2 eq), 16 h | 89:11 |
| Compound 10: PhN(SF₃)(1-naphthyl) | CH₂Cl₂, RT, 7 days, 1.0% conversion | |
| Compound 31: PhN(SF₃)CH₃ | CH₂Cl₂, RT, 5 days | 86:14 |
| Compound 35: PhN(SF₃)CH₂CH₂OMe | CH₂Cl₂, RT, EtOH(0.2 eq), 16 h | 86:14 |
| CH₃N(SF₃)CH₂CH₂OMe  37 | CH₂Cl₂, RT, EtOH(0.2 eq), 16 h | 81:19 |
| MeOCH₂CH₂N(SF₃)CH₂CH₂OMe  41 | CH₂Cl₂, 40° C., EtOH(0.2 eq), 40 h | 81:19 |

Thermal analysis studies of the newly synthesized aminosulfur trifluorides and dialkylaminosulfur trifluorides (DAST) were performed on a Radex instrument, available from Systag of Switzerland. The instrument is similar to ASTM E476-87. The instrument operates at a constant heating rate (0.5 to 2.0° C./min.) and measures heat flux into or out of a sample, in the form of a temperature difference between sample and inert reference and also the system's total internal pressure. This provides a measure of the onset of exothermic decomposition. The results of these studies provide useful information about the relative thermal stabilities of these compounds. The decomposition temperature and the quantity of gas (resultant gas pressure) produced on decomposition are important indicators of the safety in use of the compounds.

Table 10 summarizes the results of the Radex thermal analysis studies and provides a listing of decomposition temperatures, pressure gain and gas produced on two bases for the decomposition of diaryl, dialkyl, arylalkyl, and alkoxyalkylaminosulfur trifluorides (300 mg). Higher decomposition temperatures were recorded for the dialkyl compounds. Among the newly synthesized compounds, the alkoxyalkylaminosulfur trifluorides decomposed at higher temperatures than the arylalkyl and diaryl compounds.

TABLE 10

Termal analysis of aminosulfur trifluorides by Radex

| Compound | Decomposition Temp. ° C. | Pressure Gain on Decomposition (psia) | Gas Produced (psia/mmol |
|---|---|---|---|
| Et$_2$NSF$_3$ | 128 | 101 | 13 |
| Me2NSF3 | 126 | 96.6 | 33 |
| 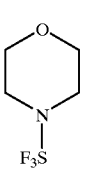 | 151 | 98.2 | 22 |
| 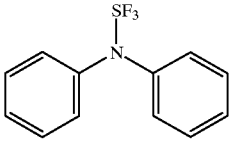 2 | 68 | 8.9 | 3 |
| 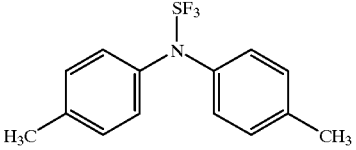 4 | 55 | 7.4 | 2 |
| 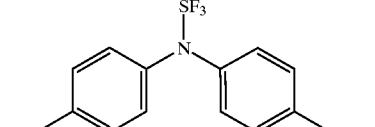 6 | 87 | 23.3 | 8 |
| 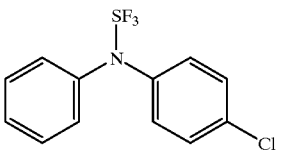 8 | 95 | 0 | 0 |

TABLE 10-continued

Termal analysis of aminosulfur trifluorides by Radex

| Compound | Decomposition Temp. °C. | Pressure Gain on Decomposition (psia) | Gas Produced (psia/mmol |
|---|---|---|---|
| 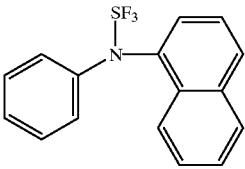 10 | 109 | 10.0 | 3 |
| 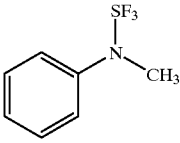 31 | 91 | 9.9 | 3 |
| 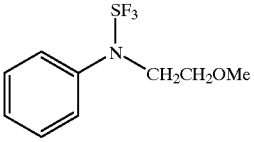 35 | 66 | 0 | 0 |
| $CH_3N(SF_3)CH_2CH_2OMe$ 37 | 104 | 1.5 | 0 |
| 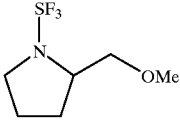 39 | 116 | 16.5 | 5 |
| $MeOCH_2CH_2N(SF_3)CH_2CH_2OMe$ 41 | 108 | 0 | 0 |

A comparison of the pressure gain on decomposition indicates that the dialkyl aminosulfur trifluorides produced a significantly larger quantity of gas as compared to the other compounds. Most of the diaryl compounds produced a relatively small quantity of gas. However, N4-chlorophenyl-N-phenylaminosulfur trifluoride was found to be remarkably stable in this regard producing no gas on decomposition. The arylalkyl compounds produced some gas on decomposition, but the alkoxyalkylaminosulfur trifluorides evolved essentially no gas at the conditions of these tests. However, the most significant factor demonstrated by the data in Table 10 is the amount of gas produced per mmol of deoxofluorination reagent tested. This is a measure of the potential for dangerous results based upon explosion of the reagent for a normalized amount of each reagent for comparison purposes. The reagents of the present invention showed significant improvement over the prior art compositions.

These results indicate that the novel aminosulfur trifluorides prepared should be much safer to use than the previously known DAST compounds. The more stable N-4-chlorophenyl-N-phenylaminosulfur trifluoride and the alkoxyalkylaminosulfur trifluorides should be especially suitable for scale-up and large scale use.

NMR spectra were obtained on a Bruker CP-300FT spectrometer operating at 282.4 MHz ($^{19}F$), 300.13 MHz ($^1H$). Chemical shifts were referenced to neat $CFCl_3(^{19}F)$ and $CHCl_3(^1H)$.

G.C.M.S. Spectra were recorded on a HP 5890 Series 11 G.C. and 5972 series mass selective detector with a HP-1 column.

EXAMPLE 1

Synthesis of Aminosulfur Trifluorides

A 3-neck, 250 mL round-bottom flask was equipped with a magnetic stirring bar, a $N_2$ inlet tube attached to dry ice condenser, a $SF_4$ gas inlet tube connected to a metal vacuum line manifold and a pressure equalized dropping funnel. The solvent (Et$_2$O or THF, 75 mL) was introduced into the flask via the dropping funnel and a 2° amine, corresponding to the products as specified below (25.0 mmol), dissolved in the solvent (Et$_2$O or THF, 25 mL) and triethylamine (3.50 mL, 25.0 mmol) were added to the dropping funnel. The condenser was cooled to −78° C. with dry ice/acetone and the solvent was cooled in like manner. A 1 liter ballast in the manifold was filled with SF$_4$ from a metal cylinder to produce a pressure of 18 psia and SF$_4$ (13 psia, 37 mmol) was introduced into the flask. The residual SF$_4$ in the ballast was pumped through a soda-lime trap. The solution of 2° amine in Et$_2$O/TEA was then added dropwise to the SF$_4$ solution and stirred. The −78° C. bath was replaced by a −10° C. bath and the mixture was stirred for 3 h. After cooling to −78° C., excess SF$_4$ was pumped out of the solution through a soda-lime trap and the solution was brought to room temperature. When Et$_2$O was used as solvent, an H-tube was attached to the flask and the solvent decanted into one arm of the H-tube. This was followed by filtration of the solution to remove precipitated TEAHF. The filtrate was then evaporated in-vacuo. After the solvent was completely removed, the H-tube was taken into a dry-box and the product was transferred to a Teflon bottle. When THF was used as solvent, an in-vacuo evaporation of the solvent was first carried out and the residue was redissolved into Et$_2$O and further processed as above $^1$H and $^{19}$F NMR of samples were done in teflon NMR tubes.

The following compounds were obtained via this procedure: diphenylaminosulfur trifluoride (2), $^1$H NMR (CDCl$_3$) δ 7.5–7.3 (m, 10H), $^{19}$F NMR (CDCl$_3$) δ 69.5 (d, 2F), 31 (t, 1F) 4,4'-dimethyl-diphenylamino-sulfur trifluoride (4). $^1$H NMR (CDCl$_3$) δ 7.35–7.10 (m, 8H), 2.35 (s, 6H). $^{19}$F NMR (CDCl$_3$) δ 68.25 (d, 2F), 32.0 (t, 1F). 4,4'-dimethoxy-diphenylaminosulfur trifluoride (6). $^1$H NMR (CDCl3) δ 7.25 (d, 4H), 7.35 (d, 4H), 3.8 (s, 6H). $^{19}$F NMR (CDCl$_3$) δ 68.5 (s, br, 2F), 31.75 (s, br, 1F) N-4-chlorophenyl-N-phenylaminosulfur trifluoride (8). $^1$H NMR (CDCl$_3$) δ 7.5–7.25 (m, 9H), $^{19}$F NMR (CDCl$_3$) δ 70 (d, 2F), 31 (t, 1F). N-naphthyl-N-phenyl-aminosulfur trifluoride (10). $^1$H NMR (CDCl$_3$) δ 8.4 (d, 0.66H), 8.15 (d, 0.34H), 7.9–6.8 (m, 11H), $^{19}$F NMR (CDCl$_3$) δ 71, 66.5 (2(d) 0.66F), 70, 67.5 (2(d), 134F) 33 (t, 1F). Indolineaminosulfur trifluoride (27). $^1$H NMR (CDCl$_3$) δ 7.4 (d, 1H), 7.2 (dd, 2H), 7.0 (d, 1H), 4.3 (t, 2H), 3.1 (t, 2H). $^{19}$F NMR (CDCl$_3$) δ 60 (br, s, 2F), 20 (br, s, 1F). 3,4-dihydro-2H-1,4-benz-oxazinesulfur trifluoride (29). $^1$H NMR (CDCl$_3$) δ 7.3–7.1 (m, 2H), 6.8–7.1 (m, 2H), 4.5–4.3 (t, 2H), 4.2–3.9 (t, 2H). $^{19}$F NMR (CDCl$_3$) δ 63 (br, s, 2F) 11 (br, s, 1F). N-methyl-N-phenylaminosulfur trifluoride (31). $^1$H NMR (CDCl$_3$) 3 7.5–7.3 (m, 3H), 7.3–7.0 (m, 2H) 3.4 (s, 3H). $^{19}$F NMR (CDCl$_3$) δ 64 (2F) δ 26 (1F). N-ethyl-N-phenyl aminosulfur trifluoride (33)[25]. N-2-methoxyethyl-N-phenylaminosulfur trifluoride (35) $^1$H NMR (CDCl$_3$) δ 7.5–7.35 (m, 3H), 7.35–7.20 (m, 2H), 4.1–3.9 (m, 2H), 3.7–3.5 (m, 2H), 3.30 (s, 3H). $^{19}$F NMR (CDCl$_3$) δ 63 (br, s, 2F), 31.5 (br, s, 1F). N-2-methoxyethyl-N-methylaminosulfur trifluoride (37). $^1$H NMR (CDCl$_3$) δ 3.8–3.3 (m, 4H), 3.15 (s, 3H), 2.95 (s, 3H). $^{19}$F NMR (CDCl$_3$) δ 56 (s, br, 2F), 23 (s, br, 1F). (S)-2-(methoxymethyl) pyrrolidin-1-yl sulfur trifluoride (39) bis (2-methoxyethyl)aminosulfur trifluoride (41) $^1$H NMR (CDCl$_3$). δ 3.5 (t, 4H), 3.15 (t, 4H), 3.05 (s, 6H). $^{19}$F NMR (CDCl$_3$) δ 55 (s, br, 2F) 28 (s, br. 1F).

EXAMPLE 2

A preparation of N-methyl-N-phenylaminosulfur trifluoride from SF$_4$(37 mmol) and N-methylaniline (25 mmol) in Et$_2$O (100 mL) using N-methylpiperidine instead of triethylamine (as above) afforded a quantitative yield of product.

EXAMPLE 3

A preparation of N-methyl-N-phenylaminosulfur trifluoride from SF$_4$(37 mmol) and N-methylaniline (25 mmol) in Et$_2$O (100 mL) using quinuclidine instead of triethylamine (as above) afforded a quantitative yield of product.

EXAMPLE 4

A preparation of N-methyl-N-phenylaminosulfur trifluoride from SF$_4$(37 mmol) and N-methylaniline (25 mmol) in Et$_2$O (100 mL) using triethylenediamine instead of triethylamine (as above)afforded a quantitative yield of product.

EXAMPLE 5

An attempted preparation of N-methyl-N-phenylaminosulfur trifluoride from SF$_4$ (37 mmol) and methylaniline (25 mmol) in Et$_2$O (100 mL) using pyridine instead of triethylamine (as in the general procedure above) produced none of the desired product.

EXAMPLE 6

An attempted preparation of bis(methoxyethyl) aminosulfur trifluoride from SF$_4$ (37 mmol) and bis (methoxyethyl)amine (25 mmol) in Et$_2$O (100 mL) using 3-methylpyridine instead of triethylamine (as in the general procedure above) gave none of the desired product.

EXAMPLE 7

An attempted preparation of N-methyl-N-phenylaminosulfur trifluoride from SF$_4$ (37 mmol) and methylaniline (25 mmol) in Et$_2$O (100 mL) using anhydrous NaF (100 mmol) instead of triethylamine (as in the general procedure above) produced none of the desired product.

EXAMPLE 8

An attempted preparation of diphenylaminosulfur trifluoride from SF$_4$ (37 mmol) and diphenylamine (25 mmol) in Et$_2$O (100 mL) using anhydrous CsF (100 mmol)instead of triethylamine (as in the general procedure above) produced none of the desired product

EXAMPLE 9

Reaction of Cyclooctanol with the New Aminosulfur Trifluorides

A solution of cyclooctanol (128 mg, 1 mmol) in CH$_2$Cl$_2$ (3.0 mL) was added to a solution of aminosulfur trifluoride per Table 8 (1 mmol) in CH$_2$Cl$_2$ (2.0 mL) at −78° C. under N$_2$ in a 3-neck flask equipped with N$_2$ inlet, septum, and a magnetic stirring bar. The reaction was monitored by G.C.M.S. for disappearance of the starting material. On completion, the mixture was poured into satd. NaHCO$_3$ (25 mL) and after CO$_2$ evolution ceased, it was extracted into CH$_2$Cl$_2$ (3×15 mL), dried (Na$_2$SO$_4$), filtered and evaporated in vacuo to obtain the product as a mixture of cyclooctyl fluoride and cyclooctene. Flash chromatography on silica gel in hexane afforded the pure products.

EXAMPLE 10

Reaction of 4-t-Butylcyclohexanone with Aminosulfur Trifluorides

A solution of 4-t-butylcyclohexanone (1.0 mmol) in $CH_2Cl_2$ (3.0 mL) contained in a 25 mL teflon vessel equipped with a swagelok stopper, $N_2$ inlet tube, and stirring bar was treated with a solution of aminosulfur trifluoride per Table 9 (1.8 mmol) in $CH_2Cl_2$ (2.0 mL) at room temperature. EtOH (11 mg, 14 µL, 0.2 mmol) was added and the mixture was stirred at room temperature. The progress of the reaction was monitored by a G.C.M.S. On completion, the solution was poured into satd. $NaHCO_3$ and after $CO_2$ evolution ceased, it was extracted into $CH_2Cl_2$ (3×15 mL), dried ($Na_2SO_4$), filtered, and evaporated in vacuo to afford a mixture of 4-t-butyl-difluorocyclohexane and 4-t-butyl-1-fluorocyclohexene.

A convenient and economically attractive method for deoxofluorination of the alcohol (cyclooctanol) and ketone (4-t-butylcyclohexanone) was achieved by conducting the reaction in the medium used for preparation of the reagent, i.e., without isolating the aminosulfur trifluoride.

Schematic representation of the in-situ fluorination process:

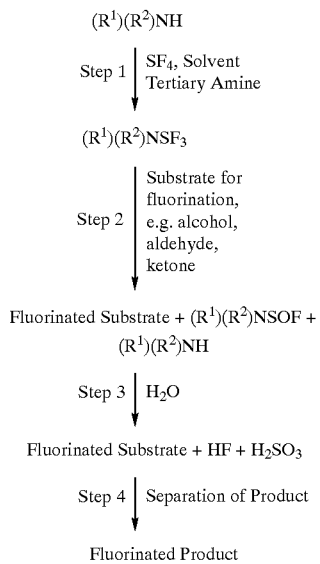

EXAMPLE 11

Deoxofluorination Conducted In-Situ without Isolation of Aminosulfur Trifluoride A solution of diphenylamine (25 mmol) in THF (25 mL) containing triethylamine (3.48 mL, 25 mmol) was added dropwise to a solution of $SF_4$ (37 mmol) in THF (75 mL) contained in a 3-neck flask equipped with a stirring bar, $N_2$ inlet tube, dry ice condenser, and $SF_4$ inlet tube (as described above) at −78° C. The mixture was brought to −10° C. and kept for 3 h. It was again cooled to −78° C. and excess $SF_4$ was removed in-vacuo. The mixture was then treated with a THF (10 mL) solution of cyclooctanol (3.20 g, 25.0 mmol) and stirred at −78° C. for 1 h. The reaction was quenched with 5 mL $H_2O$ and the solvents were evaporated in-vacuo, treated with satd. $NaHCO_3$ (200 mL), extracted into EtOAc, dried ($MgSO_4$), filtered, and evaporated in-vacuo to obtain the product as a mixture of cyclooctyl fluoride and cyclooctene (70:30 ratio).

EXAMPLE 12

A solution of diphenylaminosulfur trifluoride (25 mmol) in THF (100 mL) prepared as above was treated with a THF solution (10 mL) of 4-t-butylcyclohexanone (3.85 g, 25 mmol) at room temperature and stirred for 7 days. After work-up as described for the alcohol above, a product was obtained which was a mixture of 4-t-butyl-difluorocyclohexane and 4-t-butyl-1-fluorocyclohexene (96:4 ratio).

The present invention provides a high yielding one-step process for the preparation of a number of classes of novel aminosulfur trifluoride compounds. These novel aminosulfur trifluoride compounds have been shown to have unique performance for effecting deoxofluorination of alcohols and ketones as demonstrated by the presently reported thermal analysis studies indicating that they are safer to use than the currently available dialkylaminosulfur trifluorides (DAST), see the data in Table 10 for gas pressure generated per millimole of reagent decomposed, and more effective at fluorinating alcohols than (S)-2-(methoxyethyl) pyrrolidin-1-yl sulfur trifluoride, see Table 8 for the efficiency of fluorination showing poor fluorination by the latter compound in contrast to the compounds of the present invention.

The simplicity of the method used for preparing the new aminosulfur trifluorides combined with their safety and simplicity in use should make these compounds attractive for large scale commercial production and use, providing unexpected improvement in fluorination technology in contrast to the industry avoidance of DAST for such fluorinations.

The present invention has been set forth with regard to several preferred embodiments, but the full scope of the present invention should be ascertained from the claims which follow.

What is claimed is:

1. An aminosulfur trifluoride composition having a structure with one or more:

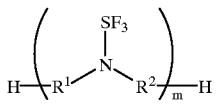

wherein m=1–5 and $R^1$ and $R^2$ are:
(1) when m=1, individually aryl or meta- or para-substituted aryl radicals in which the meta- or para-substitution is selected from the group consisting of normal and branched $C_{1-10}$, trifluoromethyl, alkoxy, aryl $C_{6-10}$, nitro, sulfonic ester, N,N-dialkylamino and halogens; or
(2) when m=1, individually aryl radicals which are fused or linked to one another; or (3) when m=1, one of $R^1$ and $R^2$ is an aryl radical and the other is an at least 5 member saturated cyclic hydrocarbon radical having zero to three heteroatoms selected from the group consisting of oxygen, nitrogen and mixtures thereof; or (4) when m=1, one of $R^1$ and $R^2$ is an aryl radical and the other is an at least 5 member saturated cyclic hydrocarbon radical having zero to three heteroatoms selected from the group consisting of oxygen, nitrogen and mixtures thereof wherein said cyclic hydrocarbon radical is fused to said aryl radical; or (5) when m=1, together a cyclic ring having 2 to 10 carbon ring members and an additional 1 heteroatom selected from the group consisting of oxygen, nitrogen and alkylated nitrogen wherein said ring has 1 to 2 alkoxyalkyl functionalities; or (6) when m=1, together an unsaturated cyclic ring having 2 to 4 carbon ring members and one to three additional heteroatoms selected from the group consisting of oxygen, nitrogen, protonated nitrogen and alkylated nitrogen wherein said ring has one to three functional groups selected from hydrogen, normal and branched $C_{1-10}$ alkyl, haloalkyl, alkoxy, aryl halogen, cyano, nitro and amino; or (7) when m=2–5, $R^1$ is a single phenyl radical linked to each —$NSF_3$ radical and $R^2$ is an aryl radical having $C_6$ to $C_{10}$; or (8) when m=2–5, $R^1$ and $R^2$ are individually divalent aryl radicals of $C_6$ to $C_{10}$ linked to adjacent —$NSF_3$ radicals except $R^1$ and $R^2$ are monovalent aryl radicals having $C_6$ to $C_{10}$ where $R^1$ and $R^2$ are linked to only one —$NSF_3$ radical.

2. The composition of claim 1 wherein m=1 and $R^1$ and $R^2$ are individually aryl and para-substituted aryl radicals in which the para-substitution is selected from the group consisting of normal and branched $C_{1-10}$ alkyl, trifluoromethyl, alkoxy, aryl $C_{6-10}$, nitro, sulfonic ester, N,N-dialkylamino and halogens.

3. The composition of claim 1 wherein said aryl radical is selected from the group consisting of a six carbon membered aromatic ring, a ten carbon membered aromatic fused ring and mixtures thereof.

4. The composition of claim 1 wherein said meta- or para-substituted aryl radical is substituted with a group selected from the group consisting of an alkyl radical of $C_1$ to $C_{10}$ in a normal or branched structure, an alkoxy radical, halogens and mixtures thereof.

5. The composition of claim 4 wherein the aryl radical of the para-substituted aryl radical is selected from the group consisting of a six carbon membered aromatic ring, a ten carbon membered aromatic fused ring and mixtures thereof.

6. The composition of claim 1 having the structure:

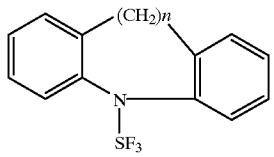

where n=2–6.

7. The composition of claim 1 having the structure:

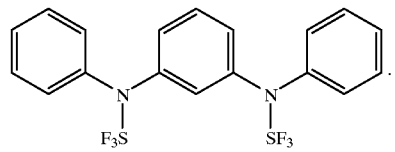

8. The composition of claim 1 having the structure:

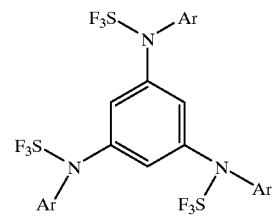

where Ar is an aryl radical of $C_6$ to $C_{10}$.

9. The composition of claim 1 having the structure:

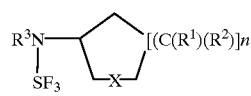

wherein $R^3$ is an aryl radical of $C_6$ to $C_{10}$, n=1–5, $R^1$ and $R^2$ are individually H or alkyl $C_{1-10}$ and X=zero to three ring element substitutions of O or $NR^4$ where $R^4$=H, normal or branched alkyl $C_{1-10}$.

10. The composition of claim 1 having the structure:

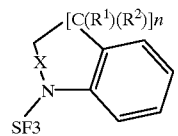

wherein $R^1$ and $R^2$=individually H or normal or branched alkyl $C_{1-10}$, n=1–5 and X=zero to three ring element substitutions of O or $NR^3$ where $R^3$=H, normal or branched alkyl $C_{1-10}$.

11. The composition of claim 1 having the structure:

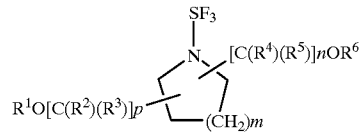

wherein $R^1$ and $R^6$ are individually normal or branched alkyl $C_{1-10}$, $R^{2-5}$, are individually H, or normal or branched alkyl $C_{1-10}$, m=1–10, n=1–10, and p=1–10.

12. The composition of claim 1 having the structure:

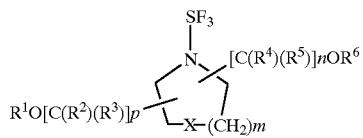

wherein $R^1$ and $R^6$ are individually normal or branched alkyl $C_{1-10}$, $R^{2-5}$, are individually H, or normal or branched alkyl $C_{1-10}$, m=1–10, n=1–10, and p=1–10, and X=a ring element substitution of O or $NR^7$ where $R^7$=H, normal or branched alkyl $C_{1-10}$.

13. The composition of claim 1 having the structure:

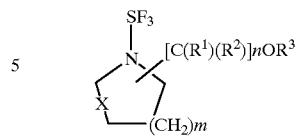

where m=1–10, n=1–10, $R^1$ and $R^2$=individually H, or normal or branched alkyl $C_{1-10}$, $R^3$=normal or branched $C_{1-10}$ and X=a ring element substitution of O, $NR^4$ where $R^4$=normal or branched alkyl $C_{1-10}$.

* * * * *